April 29, 1975 A. L. SAVELLA Plant Pat. 3,709
RHODODENDRON PLANT
Filed March 7, 1974
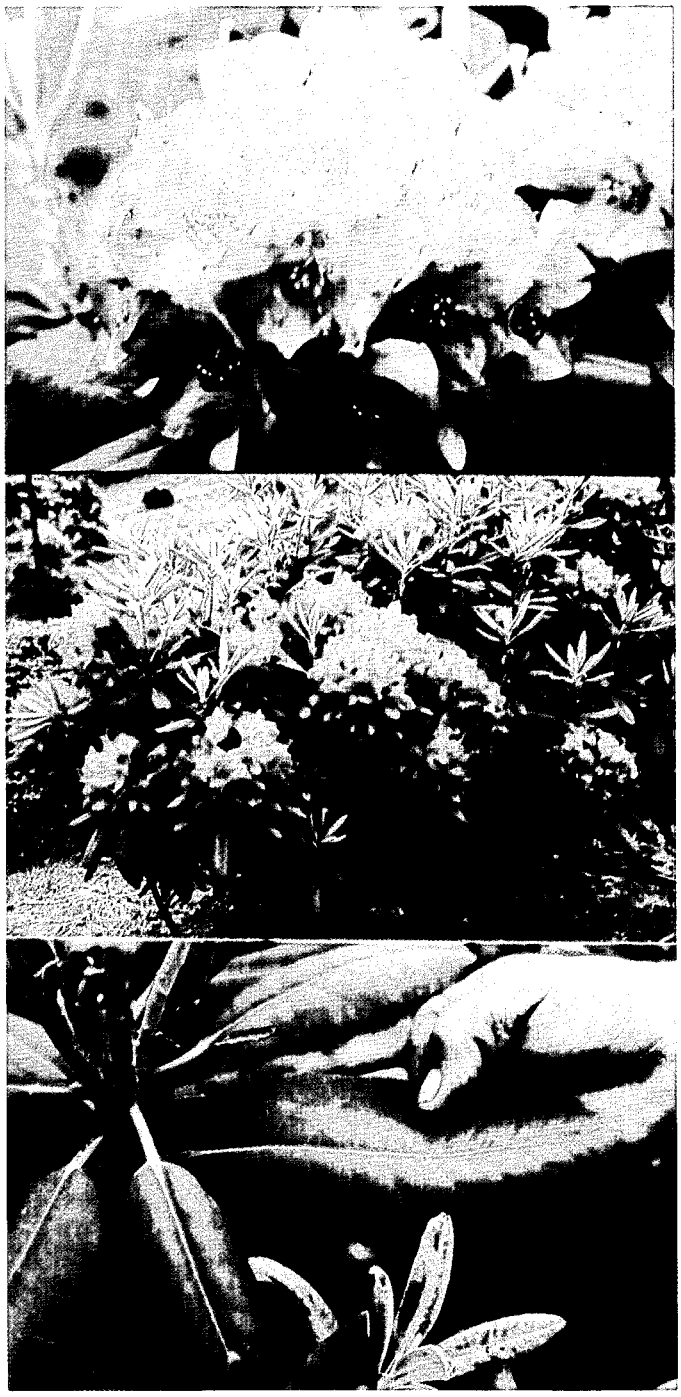

United States Patent

Plant Pat. 3,709

Patented Apr. 29, 1975

3,709

RHODODENDRON PLANT

Angelo L. Savella, Cranston, R.I., assignor to Bald Hill Research, Inc., Exeter, R.I.

Filed Mar. 7, 1974, Ser. No. 449,068

Int. Cl. A01h *5/00*

U.S. Cl. Plt.—57 1 Claim

The present invention relates to a new and distinct variety of Rhododendron plant which was originated and developed by me as a selected cultivated hybrid seedling derived from crosses of the Rhododendron variety known as "Britannia" (unpatented) with the variety known as "Dexter Hybrid 202" (unpatented).

As the result of this breeding, I have produced a new and improved Rhododendron variety which is distinguished from its parents, as well as from all other varieties, as evidenced by the following unique combination of principal characteristics which are outstanding therein:

(1) A vigorous and branching habit of growth;
(2) Large leaves which are borne on leaf stems which have a reddish tint;
(3) The ability to set flowers at an early age, usually in the second year when grown from cuttings planted in containers;
(4) An early blooming habit, usually from 1 to 2 weeks before most Catawbiense hybrids;
(5) Large flower clusters averaging 22 florets per cluster and with the individual florets ranging from 2½ inches to 3 inches in diameter;
(6) A clear, vivid scarlet red flower color which is completely free of blue tones that are characteristic of most other commercial red-flowered varieties in the Northeast, such as "America," "Nova Zembla," etc. (all unpatented);
(7) Excellent hardiness to temperatures as low as −10° F. without injury to buds or foliage; and
(8) Good resistance to Rhododendron diseases common in the Northeast, and particularly free of root rot diseases.

Asexual reproduction of my new variety by grafting and by rooted cuttings, as performed by me in my nurseries at Exeter, R.I., shows that the foregoing characteristics and distinctions come true and are established and transmitted through succeeding propagations.

The accompanying drawing shows typical specimen plants of my new Rhododendron variety, as well as close-up views on a larger scale than that of the plants, more clearly illustrating the details of the flowers and foliage, all as depicted in color as nearly true as it is reasonably possible to make the same in an illustration of this character.

The foregoing is a detailed description of my new variety, with color terminology in accordance with the Nickerson Color Fan, published by Munsell Color Corporation, of Baltimore, Md., except where general color terms of ordinary dictionary significance are obvious:

Parentage: A selected hybrid seedling of "Britannia" × "Dexter Hybrid 202."

Propagation: Holds its distinguishing characteristics through succeeding propagations by grafting and cuttings.

Locality where grown and observed: Pontiac, R.I.

Plant:

*Form.*—Bush; upright.
*Growth habit.*—Vigorous; branching.
*Rooting habit.*—Coordinate.

*Blooming habit.*—Blooms profusely at an early age, usually beginning with the second year.
*Blooming season.*—From about the middle to the end of the month of May, in Rhode Island.
*Suitability for forcing.*—Excellent.

Foliage:

*Size.*—Large leaves; borne on reddish stems. Length—from about 5 inches to 7½ inches long. Width—from about 2 inches to 3¾ inches at widest point.
*Quantity.*—Normal abundance.
*Color.*—New foliage—Upper side—Strong Yellow Green, Color No. 2.5 GY 6/8. Under side—Strong Greenish Yellow, Color No. 10 Y 7/9. Old foliage—Upper side—Moderate Yellow Green, Color No. 5 GY 5/6. Under side—Dark Yellowish Green, Color No. 10 Y 6/7.
*Shape.*—Oval pointed.
*Texture.*—Upper side—leathery. Under side—smooth.
*Margin.*—Smooth edge.
*Aspect.*—Lateral; semi-drooping.

Disease resistance: Good resistance to Rhododendron diseases common in the Northeast, and particularly free of root rot diseases, as determined by comparison with other varieties grown under the same conditions in Rhode Island.

Flowers: Staminate; borne in clustres having from 17 to 26 florets per cluster.

*Size (florets).*—Average about 2½ inches in diameter.
*Form.*—Simple corymb.
*Color.*—Clear, vivid scarlet red, near strong Red, Color No. 5 R 4/12 but brighter and free of blue tones.
*Blooming period.*—From about middle to end of May in Rhode Island.

Fruit:

*Shape.*—Capsule.
*Color.*—Brown.
*Fruiting season.*—From August to October.

Hardiness: To at least −10° F. without injury in zone 6.

I claim:

1. A new and distinct variety of Rhododendron plant, substantially as herein shown and described, characterized particularly as to novelty by the unique combination of a vigorous and branching habit of growth, large leaves which are borne on leaf stems which have a reddish tint, the ability to set flowers at an early age, usually in the second year when grown from cuttings in containers, an early blooming habit, usually from 1 to 2 weeks before most Catawbiense hybrids, large flower clusters averaging 22 florets per cluster and with the individual florets ranging from 2½ inches to 3 inches in diameter, a clear, vivid scarlet red flower color which is completely free of blue tones that are characteristic of most other commercial red-flowered varieties in the Northeast, such as "America," "Nova Zembla," etc. (all unpatented), excellent hardiness to temperatures as low as −10° F. without injury to buds or foliage, and good resistance to Rhododendron diseases common in the Northeast, and particularly free of root rot diseases.

No references cited.

ROBERT E. BAGWILL, Primary Examiner